United States Patent
Morrisroe

(10) Patent No.: US 9,433,072 B2
(45) Date of Patent: Aug. 30, 2016

(54) OXIDATION RESISTANT INDUCTION DEVICES

(71) Applicant: PERKINELMER HEALTH SCIENCES, INC., Waltham, MA (US)

(72) Inventor: Peter J Morrisroe, New Milford, CT (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 14 days.

(21) Appl. No.: 14/335,999

(22) Filed: Jul. 21, 2014

(65) Prior Publication Data

US 2015/0048061 A1 Feb. 19, 2015

Related U.S. Application Data

(63) Continuation of application No. 13/100,490, filed on May 4, 2011, now Pat. No. 8,786,394.

(60) Provisional application No. 61/331,627, filed on May 5, 2010.

(51) Int. Cl.
| | |
|---|---|
| *H01F 5/00* | (2006.01) |
| *H05H 1/30* | (2006.01) |
| *G01N 21/31* | (2006.01) |
| *G01N 21/73* | (2006.01) |
| *H01F 27/23* | (2006.01) |

(52) U.S. Cl.
CPC .............. *H05H 1/30* (2013.01); *G01N 21/3103* (2013.01); *G01N 21/73* (2013.01); *H01F 5/00* (2013.01); *H01F 27/23* (2013.01)

(58) Field of Classification Search
CPC .......... H01F 5/00; H01F 27/00–27/30; B23K 9/00–9/02; B23K 26/00; H05B 3/06
USPC ................ 336/65, 200, 232; 219/121.52
See application file for complete search history.

(56) References Cited

U.S. PATENT DOCUMENTS

| | | | | |
|---|---|---|---|---|
| 5,676,863 A | * | 10/1997 | Jouvenel | C03B 37/01291 219/121.43 |
| 2006/0286492 A1 | * | 12/2006 | Morrisroe | F23C 99/001 431/2 |

* cited by examiner

*Primary Examiner* — Tuyen Nguyen

(74) *Attorney, Agent, or Firm* — Rhodes IP PLC; Christopher R Rhodes

(57) ABSTRACT

Certain embodiments described herein are directed to induction devices comprising an oxidation resistant material. In certain examples, the induction device comprises a coil of wire that is produced from the oxidation resistant material. In some examples, the oxidation resistant induction device can be used to sustain an inductively coupled plasma in a torch.

20 Claims, 8 Drawing Sheets

500

550

535

540

Detection Device

Atomization Device 510  520  525  530

OXIDATION RESISTANT INDUCTION DEVICES

PRIORITY CLAIM

This application claims priority to, and the benefit of, U.S. Provisional Application No. 61/331,627 filed on May 5, 2010, the entire disclosure of which is hereby incorporated herein by reference for all purposes.

TECHNOLOGICAL FIELD

Certain features, aspect and embodiments are directed to oxidation resistant induction devices. In particular, certain embodiments described herein are directed to devices that can generate and/or sustain a plasma using an oxidation resistant induction coil consisting essentially of aluminum or consisting essentially of an aluminum alloy.

BACKGROUND

Plasmas are gaseous materials that include ionized species. To generate and/or sustain a plasma, a copper induction coil is typically used. The copper induction coil oxidizes quickly to copper oxide, which alters the performance of the induction coil, can lead to errors in analysis using plasma based instruments, and can lead to failure of the induction coil.

SUMMARY

In one aspect, an induction device comprising an oxidant resistant material and configured to receive a torch to sustain a plasma in the torch by providing radio frequency energy to the torch is described.

In certain embodiments, the oxidation resistant material comprises a non-coated material. In some examples, the non-coated material comprises an aluminum alloy, consists essentially of an aluminum alloy or consists of an aluminum alloy. In some embodiments, the oxidation resistant material is selected to provide an overall electrode potential that is negative when the oxidation resistant material is reacted with oxygen. In other embodiments, the oxidation resistant material is effective to sustain the plasma in the torch for at least ten hours without substantial oxidation of the material. In some examples, the induction device comprises an induction coil that is configured to surround the torch. In additional examples, the induction device is configured as a plate electrode comprising a central cavity configured to receive the torch. In other examples, the induction device consists essentially of aluminum or an aluminum alloy. In some embodiments, the oxidation resistant material is electrically coupled to a radio frequency source. In additional embodiments, the induction device comprises at least 97% by weight of the oxidation resistant material.

In another aspect, an induction device comprising an oxidant resistant paramagnetic material and configured to receive a torch to sustain a plasma in the torch by providing radio frequency energy to the torch is provided.

In certain embodiments, the oxidation resistant paramagnetic material comprises a non-coated material. In some embodiments, the non-coated paramagnetic material comprises an aluminum alloy, consists essentially of an aluminum alloy or consists of an aluminum alloy. In some examples, the oxidation resistant paramagnetic material is selected to provide an overall electrode potential that is negative when the oxidation resistant paramagnetic material is reacted with oxygen. In additional examples, the oxidation resistant paramagnetic material is effective to sustain a plasma in the torch for at least ten hours without substantial oxidation of the material. In some embodiments, the induction device comprises an induction coil that is configured to surround the torch. In other embodiments, the induction device is configured as a plate electrode comprising a central cavity configured to receive the torch. In some embodiments, the induction device consists essentially of aluminum. In other embodiments, the induction device consists essentially of platinum. In additional embodiments, the oxidation resistant paramagnetic material is electrically coupled to a radio frequency source.

In an additional aspect, a torch assembly comprising a torch body, and an induction device comprising an oxidant resistant material and configured to receive the torch body to sustain a plasma in the torch body by providing radio frequency energy to the torch body is disclosed.

In certain embodiments, the oxidation resistant material comprises a non-coated material. In some embodiments, the non-coated material comprises an aluminum alloy, consists essentially of an aluminum alloy or consists of an aluminum alloy. In some examples, the oxidation resistant material is an oxidation resistant paramagnetic material. In other examples, the oxidation resistant material is effective to sustain a plasma in the torch for at least ten hours without substantial oxidation of the material. In additional examples, the induction device comprises an induction coil that is configured to surround the torch. In certain examples, the induction device is configured as a plate electrode comprising a central cavity configured to receive the torch. In some examples, the induction device consists essentially of aluminum. In other examples, the induction device is electrically coupled to a radio frequency source. In some examples, the induction device comprises at least 97% by weight of the oxidation resistant material.

In an another aspect, an optical emission device comprising a torch body configured to sustain an inductively coupled plasma, an induction device comprising an oxidation resistant material and configured to provide radio frequency energy to the torch body to sustain the plasma in the torch body, and an optical detector configured to detect optical emission of species provided to the inductively coupled plasma is described.

In certain examples, the induction device comprises an aluminum alloy, consists essentially of an aluminum alloy or consists of an aluminum alloy. In some examples, the induction device consists essentially of an oxidation resistant paramagnetic material. In other examples, the optical detector comprises a photomultiplier tube or a grating. In some embodiments, the optical emission device can further include a radio frequency generator electrically coupled to the induction device.

In an additional aspect, an atomic absorption device comprising a torch body configured to sustain an inductively coupled plasma, an induction device comprising an oxidation resistant material and configured to provide radio frequency energy to the torch body to sustain the plasma in the torch body, a light source configured to provide light to excite species provided to the inductively coupled plasma, and a detector configured to detect the excited species is provided.

In certain embodiments, the induction device comprises an aluminum alloy, consists essentially of an aluminum alloy or consists of an aluminum alloy. In some examples, the induction device consists essentially of an oxidation resistant paramagnetic material. In other examples, the optical detector comprises a photomultiplier tube or a grating. In additional examples, the optical emission device can also include a radio frequency generator electrically coupled to the induction device.

In another aspect, a mass spectrometer comprising a torch body configured to sustain an inductively coupled plasma, an induction device comprising an oxidation resistant material and configured to provide radio frequency energy to the torch body to sustain the plasma in the torch body, and a mass analyzer in fluid communication with the chamber and configured to separate species based on mass-to-charge ratios is described.

In certain examples, the induction device comprises an aluminum alloy, consists essentially of an aluminum alloy or consists of an aluminum alloy. In some examples, the induction device comprises an oxidation resistant paramagnetic material, consists essentially of an oxidation resistant paramagnetic material or consists of an oxidation resistant paramagnetic material. In some embodiments, the mass spectrometer comprises a radio frequency generator electrically coupled to the induction device. In certain examples, the mass spectrometer can be coupled to another mass spectrometer. In some examples, the mass spectrometer can be coupled to a gas chromatography system. In certain embodiments, the induction device comprises at least 97% by weight of the oxidation resistant material. In other embodiments, the inductive device comprises a non-coated material. In additional embodiments, the oxidation resistant material is effective to sustain the plasma in the torch for at least ten hours without substantial oxidation of the material.

In an additional aspect, a method of generating a plasma comprising introducing a gas into a torch body, providing radio frequency energy to the torch using an induction device comprising an oxidation resistant material, and igniting the gas in the torch body to generate the plasma is disclosed.

In certain examples, the induction device comprises a non-coated oxidation resistant material. In other examples, the induction device comprises an aluminum alloy, consists essentially of an aluminum alloy, or consists of an aluminum alloy. In additional examples, the method can include sustaining the plasma in the torch body for at least ten hours without substantial oxidation forming on the induction device. In some examples, the method can include sustaining the plasma in the torch body for at least one hundred hours without substantial oxidation forming on the induction device.

In another aspect, a method of generating a plasma comprising introducing a gas into a torch body, providing radio frequency energy to the torch using an induction device comprising an oxidation resistant paramagnetic material, and igniting the gas in the torch body to generate the plasma is provided.

In certain embodiments, the induction device comprises a non-coated oxidation resistant paramagnetic material. In other embodiments, the induction device comprises an aluminum alloy, consists essentially of an aluminum alloy or consists of an aluminum alloy. In some embodiments, the method can include sustaining the plasma in the torch body for at least ten hours without substantial oxidation forming on the induction device. In additional embodiments, the method can include sustaining the plasma in the torch body for at least one hundred hours without substantial oxidation forming on the induction device.

In other aspects, a method of facilitating generation of a plasma, the method comprising providing an induction device comprising an oxidation resistant material is disclosed. In some aspects, a method of facilitating generation of a plasma, the method comprising providing an induction device comprising an oxidation resistant paramagnetic material is provided. In additional aspects, a method of facilitating generation of a plasma, the method comprising providing an induction device consisting essentially of an oxidation resistant material is described. In some aspects, a method of facilitating generation of a plasma, the method comprising providing an induction device consisting essentially of an oxidation resistant paramagnetic material is disclosed. In other aspects, a method of facilitating generation of a plasma, the method comprising providing an induction device consisting of an oxidation resistant material is provided. In certain aspects, a method of facilitating generation of a plasma, the method comprising providing an induction device consisting of an oxidation resistant paramagnetic material is described. In additional aspects, a method of facilitating generation of a plasma, the method comprising providing an induction device comprising an aluminum alloy is provided. In some aspects, a method of facilitating generation of a plasma, the method comprising providing an induction device comprising aluminum is disclosed. In additional aspects, a method of facilitating generation of a plasma, the method comprising providing an induction device consisting essentially of an aluminum alloy is provided. In other aspects, a method of facilitating generation of a plasma, the method comprising providing an induction device consisting essentially of aluminum is disclosed. In additional aspects, a method of facilitating generation of a plasma, the method comprising providing an induction device consisting of an aluminum alloy is provided. In some aspects, a method of facilitating generation of a plasma, the method comprising providing an induction device consisting of aluminum is described.

Additional aspects, features, embodiments, and examples are described in more detail below.

BRIEF DESCRIPTION OF THE FIGURES

Certain illustrative embodiments are described in more detail below with reference to the accompanying figures in which:

FIG. 5 is an block diagram of an optical emission device, in accordance with certain examples;

Figure 1:
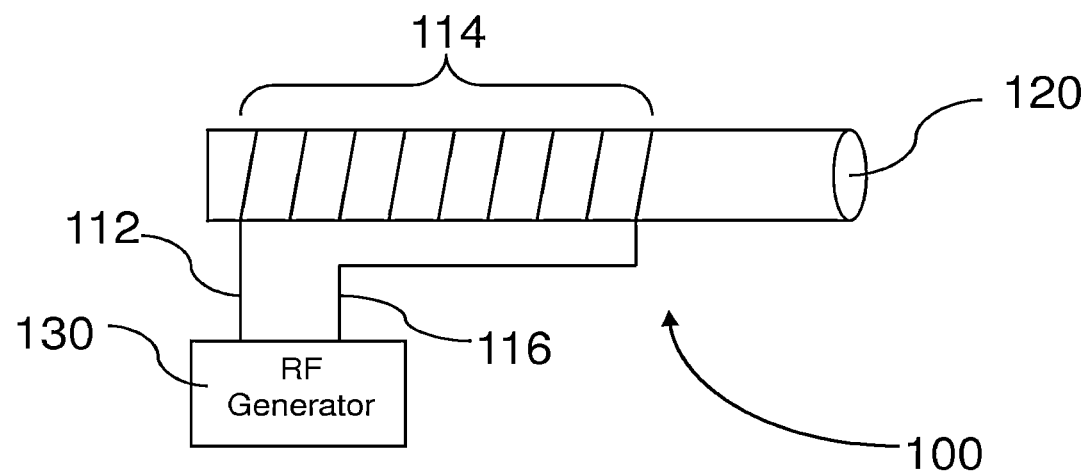
FIG. 1 is an illustration of an induction coil surrounding a torch, in accordance with certain examples.

Certain figures show and the description herein may refer in certain instances to coiled structures. Where an induction device comprising coils is used, the number of turns in the coil can vary depending on the desired plasma or the desired instrument set-up. In addition, the gas parameters, species to be analyzed and the like can vary depending on the desired analysis to be performed. It will be within the ability of the person of ordinary skill in the art, given the benefit of this disclosure, to select suitable operating parameters for use with the oxidation resistant induction devices described herein.

DETAILED DESCRIPTION

Certain embodiments described herein include are directed to devices including an oxidation resistant induction device. In certain examples, the oxidation resistant induction device can be used in plasma based devices and can resist oxidation commonly encountered with existing induction coils made from copper. Embodiments of the oxidation resistant devices can provide an increased lifetime while still providing suitable energy to sustain and/or generate an inductively coupled plasma.

In certain examples, the oxidation resistant induction devices described herein can take many different forms. For example, the induction device can take the form of a coil of wire electrically coupled to a radio frequency (RF) generator and/or radio frequency transmitter. In other examples, the oxidation resistant induction device can take the form of one or more plates, e.g., circular or rectangular plates, or circular coils in electrical communication with a RF generator. In some examples, the induction device can be constructed by placing a coil of wire, made from an oxidation resistant material, in electrical communication with a radio frequency generator. The coil of wire may be wrapped around a chamber, e.g., a torch body, to supply radio frequency energy to the chamber. In embodiments where the oxidation resistant induction device takes the form of a coil, the oxidation resistant induction devices are referred to herein as an induction coil or a load coil. In other examples, however, the induction device can take the form of a plate electrode. Where a plate electrode is used, the plate electrode can be used by itself or can be used in combination with one or more additional plate electrodes, if desired.

In certain embodiments, most Inductively Coupled Plasma (ICP) generator load coils are made of copper. This copper coil oxidizes and deteriorates over time due to the high circulating radio frequency current and the proximity of the coil to the high temperature plasma. As the copper induction coil ages, the copper oxide flakes can short out the turns of the load coil causing an arc and failure of the coil. The copper oxide is also a source of sample contamination. In operation, copper oxide can form almost immediately, and after 100 hours of operation, a copper load coil shows significant oxidation. Other load coil approaches include plating copper with a conductive metal such as gold or silver. These plating's can sputter onto the torch glass resulting in improper coupling of the magnetic field to the plasma or the plating can crack causing arcing and coil failure.

In certain embodiments, the oxidation resistant induction devices described herein can be produced using an oxidation resistant material that can provide an induction device that can operate for at least 10 hours, 20 hours, 50 hours, 100 hours or more without any substantial formation of interfering oxides on surfaces of the induction device. In other examples, the oxidation resistant induction device can provide substantially the same performance characteristics as a copper induction coil without the undesirable surface oxidation on the induction device.

In certain embodiments, the induction devices described herein can include an oxidation resistant material. In certain examples, the oxidation resistant material can be a non-coated material. As described above, coatings can, for example, flake off and interfere with operation of plasma based devices. In some embodiments, it may be desirable that the oxidation resistant material used in the induction coil consist essentially of an oxidation resistant metal that is highly conductive such as, for example, aluminum, gold or silver. In some examples, the oxidation resistant material can be an alloy having minor amounts of an additive to increase strength. For example, the oxidation resistant material can include aluminum with a small amount of manganese or other metal to increase the strength of the coil. Illustrative materials for use in producing an oxidation resistant induction device include, but are not limited to, aluminum alloys such as, for example, 3003 series aluminum alloy (97.1% aluminum), 1000 series aluminum alloy (99.5% aluminum), or other alloys commercially available, for example, from McMaster-Carr (www.mcmaster.com). In certain embodiments, the oxidation resistant material includes, by weight, at least 95% of an oxidation resistant metal, more particularly about 96%, 97%, 98%, 99% or more of the oxidation resistant metal. In some examples, the oxidation resistant material consists essentially of aluminum, gold or silver and may include minor impurities or dopants to render the material suitable for use as an induction device. Both induction coils and plate electrodes can be used that include the material amounts specified herein.

In certain embodiments, the oxidation resistant induction device can include an oxidation resistant material that is paramagnetic. Without wishing to be bound by any particular scientific theory, the paramagnetic nature of the oxidation resistant material can alter the magnetic field provided to the plasma torch as compared to the type and nature of the magnetic field provided by a diamagnetic material. In addition, there may be many materials that exist which are oxidation resistant, e.g., those already in an oxidized form, but these materials generally are not paramagnetic and may not be suitable for use in an induction device. Illustrative types of oxidation resistant paramagnetic materials include, but are not limited to, aluminum and platinum. In certain embodiments where a paramagnetic material is used, the oxidation resistant induction device may take the form of a coiled wire that consists essentially of the oxidation resistant paramagnetic material. In some examples, the oxidation resistant induction device may be a coiled wire that includes, by weight, at least 95%, 96%, 97%, 98%, 99% or more of an oxidation resistant paramagnetic material. In other instances, the oxidation resistant induction device may take the form of a plate electrode that includes, by weight, at least 95%, 96%, 97%, 98%, 99% or more of an oxidation resistant paramagnetic material.

In certain embodiments, the oxidation resistant induction device can include a non-oxide oxidation resistant material. The non-oxide material may be aluminum, gold, platinum, silver or non-oxide alloys thereof. The oxidation resistant induction device may take the form of a coiled wire that consists essentially of the non-oxide oxidation resistant material. In some examples, the non-oxide oxidation resistant induction device may be a coiled wire that includes, by weight, at least 95%, 96%, 97%, 98%, 99% or more of the non-oxide oxidation resistant material. In other instances, the oxidation resistant induction device may take the form of a plate electrode that includes, by weight, at least 95%, 96%, 97%, 98%, 99% or more of a non-oxide oxidation resistant material.

In some embodiments, the oxidation resistant material can be, or can include, materials that would provide an overall negative electrode potential when reacted with oxygen. For example, materials can be selected, based on their half reaction electrode potential, such that when the material is reacted with oxygen, the overall electrode potential would be negative. Such materials generally can be unreactive toward oxygen and oxidation resistant. Suitable materials can be selected from physical tables and commonly available listings of half-reaction potentials.

In certain embodiments, the number of coil turns in the induction coil can vary. In some embodiments, the induction coil may include from about one-half (½) to about twenty turns, for example, about one-half (½) to about ten turns or about 1½ to about ten turns, e.g., about 2½ turns to about six turns. The induction coil can include a fitting or coupling so that the coil can be mounted and/or electrically coupled to a radio frequency generator. An illustrative induction coil is shown in FIG. 1. The device 100 includes an induction coil having a first end 112, a body 114 and a second end 116. The body 114 comprises a wire that can be wrapped around a chamber 120. The first end 112 and the second end 116 each can be electrically coupled to a radio frequency generator 130 so that radio frequency energy can be provided from the induction coil body 114 to the chamber 120 to sustain a plasma in the chamber 120. In some examples, the entire induction coil can be produced using an oxidation resistant material, whereas in other examples, only the coil body 114 that surrounds the chamber 120 includes the oxidation resistant material and the other portions of the induction coil can be produced using other conductive materials which may or may not be oxidation resistant.

Figure 2A:
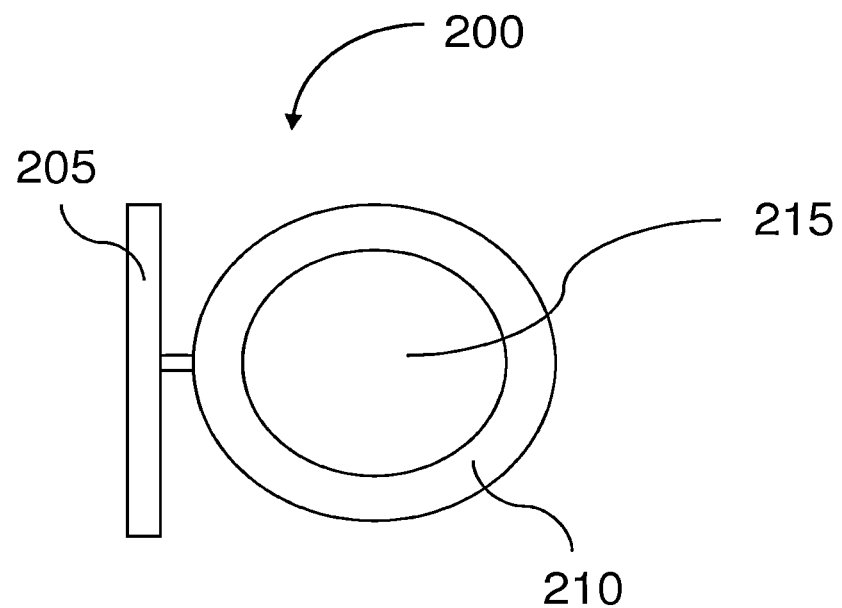
FIG. 2A is a side view of a circular induction device, in accordance with certain examples.
Figure 2B:
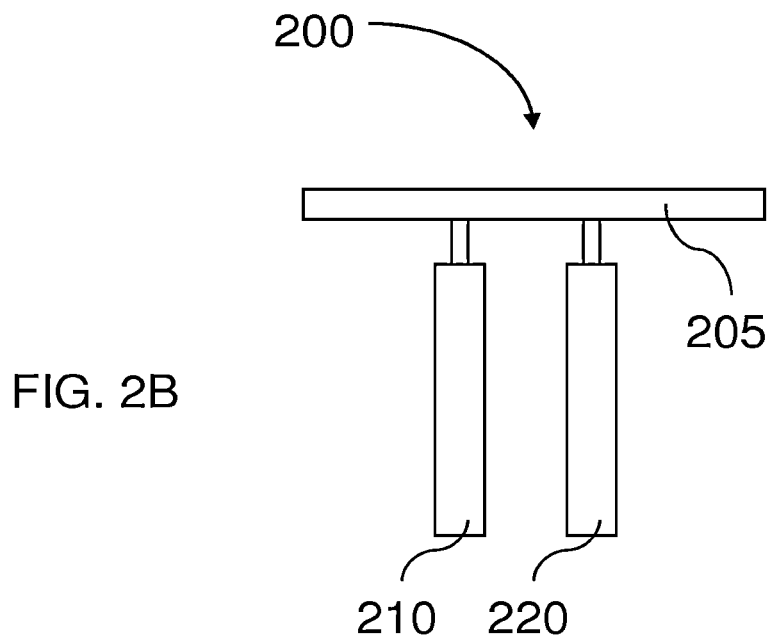
FIG. 2B is a top view of a circular induction device, in accordance with certain examples.

In certain examples, the oxidation resistant induction device can take the form of a plate induction device, e.g., a plate electrode. Referring to FIGS. 2A and 2B, an oxidation resistant induction device 200 comprises a support or plate 205, a first plate electrode 210 and a second plate electrode 220 each mounted to the support 205. Each of the first plate electrode 210 and the second plate electrode 220 may be configured to receive a chamber within the interior 215 of the electrodes. The support or plate 205 may be electrically coupled to a radio frequency transmitter or generator to provide radio frequency energy to the first plate electrode 210 and the second plate electrode 220. In this example, the first plate electrode 210 and the second plate electrode 220 may be operated at the same frequency or may be individually tuned to provide different frequencies. The configuration shown in FIGS. 2A and 2B is one where the electrodes 210 and 220 are generally circular with a central circular cavity configured to receive a chamber, e.g., a torch body. In other examples as described herein, the shape of the induction device can be a non-circular shape. In certain instances, the support 205 can be configured as a grounding plate as described, for example, in commonly owned U.S. Pat. No. 7,511,246, the entire disclosure of which is hereby incorporated herein by reference for all purposes.

Figure 3:
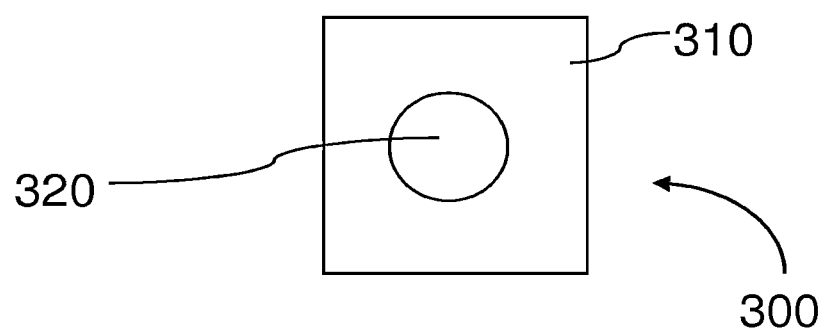
FIG. 3 is a side view of a plate induction device that is rectangular, in accordance with certain examples.

In certain embodiments and referring to FIG. 3, an induction device can include a plate electrode 300, e.g., a flat plate electrode, that includes a body 310 and a central cavity or aperture 320. While the device 300 of FIG. 3 is generally rectangular shaped, other shapes for plate electrodes such as circular, oval, elliptical and the like may also be used. The body 310 of the induction device 300 can include an oxidation resistant material such that in operation substantially no oxide forms on the surface of the induction device body 310. The central cavity 320 can be sized and arranged to receive a chamber or torch body. The plate induction device 300 can be used by itself or in combination with another electrode, e.g., another plate electrode. In some embodiments, two plate electrodes are used and are electrically coupled to a radio frequency generator source such that radio frequency energy can be provided from the plate electrodes to the chamber to sustain a plasma in the chamber. If desired, each of the plate electrodes can be electrically coupled to a grounding plate as noted herein.

Figure 4:
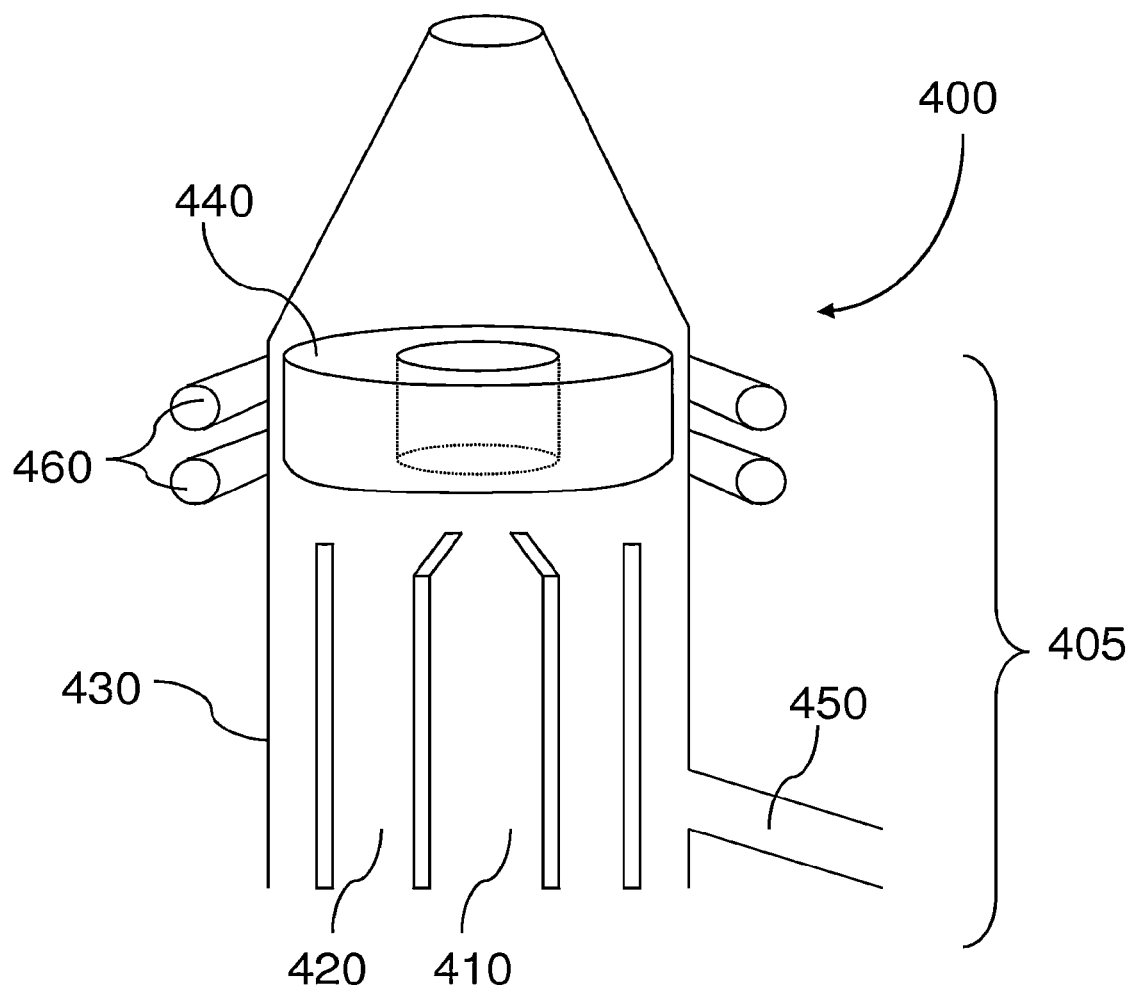
FIG. 4 is an illustration showing components used to sustain an inductively coupled plasma, in accordance with certain examples.

In certain embodiments, the oxidation resistant induction devices described herein can be used in combination with a plasma torch to sustain a plasma in the plasma torch. One configuration is shown in FIG. 4. An inductively coupled plasma device 400 includes a chamber 405 comprising three or more tubes, such as tubes 410, 420 and 430. The tube 410 is fluidically coupled to a gas source, such as argon, and a sample introduction device, e.g., a nebulizer or other device. The argon gas aerosolizes the sample and carries it into the desolvation and ionization regions of a plasma 440. The tube 420 may be configured to provide tangential gas flow throughout the tube 430 to isolate the plasma 440 from the tube 430. Without wishing to be bound by any particular scientific theory, a gas is introduced through inlet 450, and the tangential flow acts to cool the inside walls of center tube 410 and centers the plasma 440 radially. Radio frequency oxidation resistant inductions coils 460 can be electrically coupled to a radio frequency generator (not shown) and are configured to sustain the plasma 440 after the gas is ionized using an arc, spark, etc. The person of ordinary skill in the art, given the benefit of this disclosure, will be able to select or design suitable plasmas including, but not limited to, inductively coupled plasmas, direct current plasmas, microwave induced plasmas, etc., and suitable devices for generating plasmas are commercially available from numerous manufacturers including, but not limited to, PerkinElmer Health Sciences, Inc. (Waltham, Mass.), Varian Instruments, Inc. (Palo Alto, Calif.), Teledyne Leeman Labs, (Hudson, N.H.), and Spectro Analytical Instruments (Kleve, Germany).

In certain embodiments, the oxidation resistant induction devices can be used with a low flow plasma, such as those described in commonly assigned U.S. patent application Ser. No. 11/372,996, the entire disclosure of which is hereby incorporated herein by reference for all purposes. In other examples, the oxidation resistant induction devices described herein can be used with an inductively coupled and capacitively coupled plasma or with a capacitively coupled plasma.

In certain examples, the oxidation resistant induction devices described herein can be used in optical emission spectrometer (OES), as shown in FIG. 5. As chemical species are atomized and/or ionized, the outermost electrons may undergo transitions which may emit light (potentially including non-visible light). For example, when an electron of an atom is in an excited state, the electron may emit energy in the form of light as it decays to a lower energy state. Suitable wavelengths for monitoring optical emission from excited atoms and ions will be readily selected by the person of ordinary skill in the art, given the benefit of this disclosure. Exemplary optical emission wavelengths include, but are not limited to, 396.152 nm for aluminum, 193.696 nm for arsenic, 249.772 nm for boron, 313.107 nm for beryllium, 214.440 nm for cadmium, 238.892 nm for cobalt, 267.716 nm for chromium, 224.700 nm for copper, 259.939 nm for iron, 257.610 nm for manganese, 202.031 nm for molybdenum, 231.604 nm for nickel, 220.353 nm for lead, 206.836 nm for antimony, 196.206 nm for selenium, 190.801 nm for tantalum, 309.310 nm for vanadium and 206.200 nm for zinc. The exact wavelength of optical emission may be red-shifted or blue-shifted depending on the state of the species, e.g., atom, ion, etc., and depending on the difference in energy levels of the decaying electron transition, as known in the art.

Referring to FIG. 5 again, an OES device 500 includes a housing 505, a sample introduction device 510, an atomization device 520, which typically is an inductively coupled plasma, and a detection device 530. The sample introduction device 510 may vary depending on the nature of the sample. In certain examples, the sample introduction device 510 may be a nebulizer that is configured to aerosolize liquid sample for introduction into the atomization device 520. In other examples, the sample introduction device 510 may be an injector configured to receive sample that may be directly injected or introduced into the atomization device. If desired, the sample introduction device 510 can include a low-flow injector as described, for example, in commonly owned U.S. patent application Ser. No. 13/100,416 filed on May 4, 2011, the entire disclosure of which is hereby incorporated herein by reference. Other suitable devices and methods for introducing samples will be readily selected by the person of ordinary skill in the art, given the benefit of this disclosure. The atomization device 520 typically is a plasma that includes an oxidation resistant induction device as described herein. The atomization device can include a conventional Fassel torch or can include a low-flow plasma torch, if desired. Illustrative types of low flow torches are described in U.S. patent application Ser. No. 13/100,416. The detection device 530 may take numerous forms and may be any suitable device that may detect optical emissions, such as optical emission 525. For example, the detection device 530 may include suitable optics, such as lenses, mirrors, prisms, windows, band-pass filters, etc. The detection device 530 may also include gratings, such as echelle gratings, to provide a multi-channel OES device. Gratings such as echelle gratings may allow for simultaneous detection of multiple emission wavelengths. The gratings may be positioned within a monochromator or other suitable device for selection of one or more particular wavelengths to monitor. In certain examples, the detection device 530 may include a charge coupled device (CCD), a flat panel detector or other suitable types of detectors. In other examples, the OES device may be configured to implement Fourier transforms to provide simultaneous detection of multiple emission wavelengths. The detection device may be configured to monitor emission wavelengths over a large wavelength range including, but not limited to, ultraviolet, visible, near and far infrared, etc. The OES device 500 may further include suitable electronics such as a microprocessor and/or computer and suitable circuitry to provide a desired signal and/or for data acquisition. Suitable additional devices and circuitry are known in the art and may be found, for example, on commercially available OES devices such as Optima 2100DV series and Optima 5000 DV series OES devices commercially available from PerkinElmer Health Sciences, Inc. The optional amplifier 540 may be operative to increase a signal 535, e.g., amplify the signal from detected photons, and provides the signal to display 550, which may be a readout, computer, etc. In examples where the signal 535 is sufficiently large for display or detection, the amplifier 540 may be omitted. In certain examples, the amplifier 540 is a photomultiplier tube configured to receive signals from the detection device 530. Other suitable devices for amplifying signals, however, will be selected by the person of ordinary skill in the art, given the benefit of this disclosure. It will also be within the ability of the person of ordinary skill in the art, given the benefit of this disclosure, to retrofit existing OES devices with the atomization devices disclosed here and to design new OES devices using the atomization devices disclosed here. The OES devices may further include autosamplers, such as AS90 and AS93 autosamplers commercially available from PerkinElmer Health Sciences, Inc. or similar devices available from other suppliers.

In certain embodiments, the oxidation resistant induction devices described herein can be used in an atomic absorption (AA) spectrometer. Atoms and ions in or exiting the plasma may absorb certain wavelengths of light to provide energy for a transition from a lower energy level to a higher energy level. An atom or ion may contain multiple resonance lines resulting from transition from a ground state to a higher energy level. The energy needed to promote such transitions may be supplied using numerous sources, e.g., heat, flames, plasmas, arc, sparks, cathode ray lamps, lasers, etc, as discussed further below. Suitable sources for providing such energy and suitable wavelengths of light for providing such energy will be readily selected by the person of ordinary skill in the art, given the benefit of this disclosure.

Figure 6:
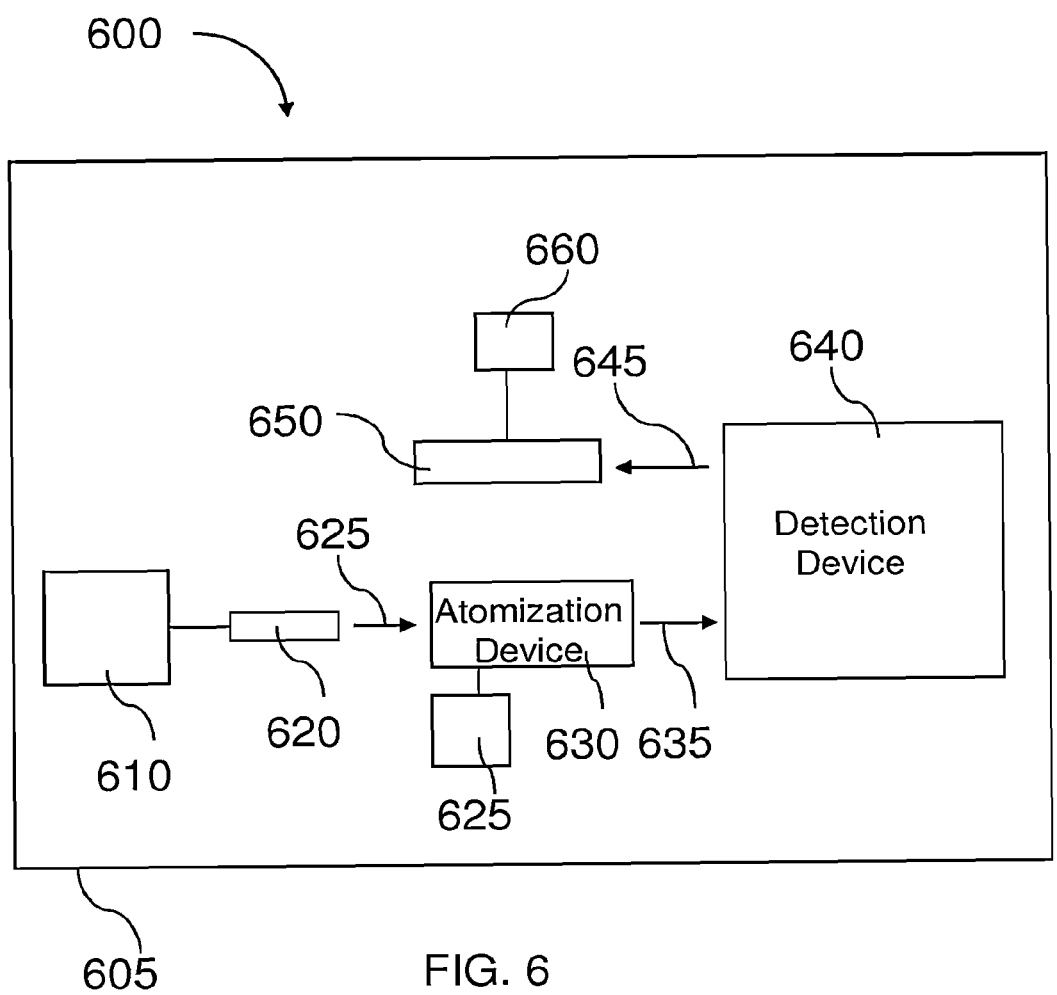
FIG. 6 is a block diagram of a single beam atomic absorption device, in accordance with certain examples.

In certain examples, an illustration of an atomic absorption spectrometer is shown in FIG. 6. The single beam AA device 600 includes a housing 605, a power source 610, a lamp 620, a sample introduction device 625, an atomization device 630, a detection device 640, an optional amplifier 650 and a display 660. The power source 610 may be configured to supply power to the lamp 620, which provides one or more wavelengths of light 622 for absorption by atoms and ions. Suitable lamps include, but are not limited to mercury lamps, cathode ray lamps, lasers, etc. The lamp may be pulsed using suitable choppers or pulsed power supplies, or in examples where a laser is implemented, the laser may be pulsed with a selected frequency, e.g., 5, 10, or 20 times/second. The exact configuration of the lamp 620 may vary. For example, the lamp 620 may provide light axially along the atomization device 630 or may provide light radially along the atomization device 630. The example shown in FIG. 6 is configured for axial supply of light from the lamp 620. There may be signal-to-noise advantages using axial viewing of signals, as described in the commonly assigned applications incorporated herein by reference. The atomization device 630 typically includes an oxidation resistant induction device and a plasma torch. As described in reference to FIG. 5, the plasma torch may be a conventional plasma torch or a low-flow plasma torch, and the sample introduction device 625 can, if desired, include or use a low-flow injector. As sample is atomized and/or ionized in the atomization device 630, the incident light 622 from the lamp 620 may excite atoms. That is, some percentage of the light 622 that is supplied by the lamp 620 may be absorbed by the atoms and ions in the atomization device 630. The remaining percentage of the light 635 may be transmitted to the detection device 640. The detection device 640 may provide one or more suitable wavelengths using, for example, prisms, lenses, gratings and other suitable devices such as those discussed above in reference to the OES devices, for example. The signal may be provided to the optional amplifier 650 for increasing the signal provided to the display 660. To account for the amount of absorption by sample in the atomization device 630, a blank, such as water, may be introduced prior to sample introduction to provide a 100% transmittance reference value. The amount of light transmitted once sample is introduced into atomization chamber may be measured, and the amount of light transmitted with sample may be divided by the reference value to obtain the transmittance. The negative $\log_{10}$ of the transmittance is equal to the absorbance. AA device 600 may further include suitable electronics such as a microprocessor and/or computer and suitable circuitry to provide a desired signal and/or for data acquisition. Suitable additional devices and circuitry may be found, for example, on commercially available AA devices such as AAnalyst series spectrometers commercially available from PerkinElmer Health Sciences, Inc. It will also be within the ability of the person of ordinary skill in the art, given the benefit of this disclosure, to retrofit existing AA devices with the atomization devices disclosed here and to design new AA devices using the atomization devices disclosed here. The AA devices may further include autosamplers known in the art, such as AS-90A, AS-90plus and AS-93plus autosamplers commercially available from PerkinElmer Health Sciences, Inc.

Figure 7:
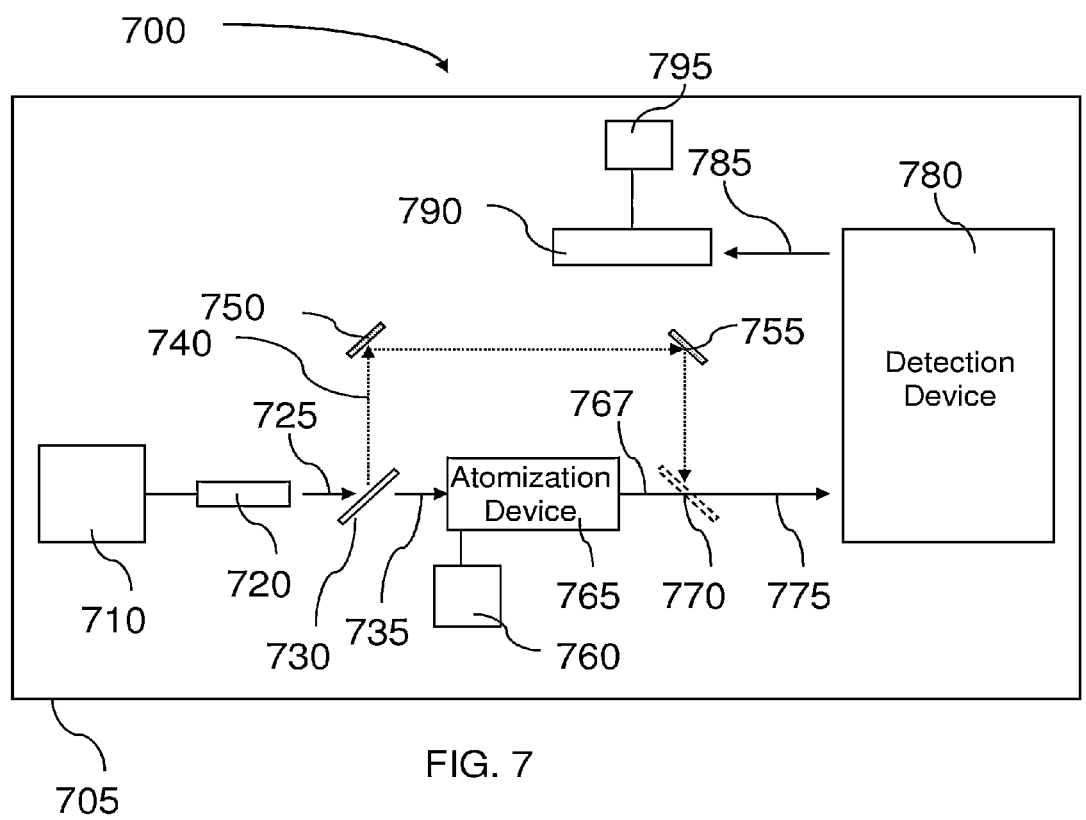
FIG. 7 is a block diagram of a dual beam atomic absorption device, in accordance with certain examples.

In certain embodiments, the oxidation resistant induction devices described herein can be used in a dual beam AA device. Referring to FIG. 7, a dual beam AA device 700 includes a housing 705, a power source 710, a lamp 720, an atomization device 765, a detection device 780, an optional amplifier 790 and a display 795. The power source 710 may be configured to supply power to the lamp 720, which provides one or more wavelengths of light 725 for absorption by atoms and ions. Suitable lamps include, but are not limited to, mercury lamps, cathode ray lamps, lasers, etc. The lamp may be pulsed using suitable choppers or pulsed power supplies, or in examples where a laser is implemented, the laser may be pulsed at a selected frequency, e.g., 5, 10 or 20 times/second. The configuration of the lamp 720 may vary. For example, the lamp 720 may provide light axially along the atomization device 765 or may provide light radially along the atomization device 765. The example shown in FIG. 7 is configured for axial supply of light from the lamp 720. As discussed above, there may be signal-to-noise advantages using axial viewing of signals. The atomization device 765 may be an inductively coupled plasma that includes an oxidation resistant induction device. If desired, the torch of the atomization device 765 may be a conventional torch or a low-flow plasma torch as described in reference to FIG. 5, and any sample introduction device (not shown) that is used may include conventional injector or a low-flow injector as described in reference to FIGS. 5 and 6. As sample is atomized and/or ionized in the atomization device 765, the incident light 725 from the lamp 720 may excite atoms. That is, some percentage of the light 725 that is supplied by the lamp 720 may be absorbed by the atoms and ions in the atomization device 765. The remaining percentage of the light 767 is transmitted to the detection device 780. In examples using dual beams, the incident light 725 may be split using a beam splitter 730 such that some percentage of light, e.g., about 10% to about 90%, may be transmitted as a light beam 735 to atomization device 765 and the remaining percentage of the light may be transmitted as a light beam 740 to lenses 750 and 755. The light beams may be recombined using a combiner 770, such as a half-silvered mirror, and a combined signal 775 may be provided to the detection device 780. The ratio between a reference value and the value for the sample may then be determined to calculate the absorbance of the sample. The detection device 780 may provide one or more suitable wavelengths using, for example, prisms, lenses, gratings and other suitable devices known in the art, such as those discussed above in reference to the OES devices, for example. Signal 785 may be provided to the optional amplifier 790 for increasing the signal for provide to the display 795. AA device 700 may further include suitable electronics known in the art, such as a microprocessor and/or computer and suitable circuitry to provide a desired signal and/or for data acquisition. Suitable additional devices and circuitry may be found, for example, on commercially available AA devices such as AAnalyst series spectrometers commercially available from PerkinElmer Health Sciences, Inc. It will be within the ability of the person of ordinary skill in the art, given the benefit of this disclosure, to retrofit existing dual beam AA devices with the induction devices disclosed here and to design new dual beam AA devices using the induction devices disclosed here. The AA devices may further include autosamplers known in the art, such as AS-90A, AS-90plus and AS-93plus autosamplers commercially available from PerkinElmer Health Sciences, Inc.

Figure 8:
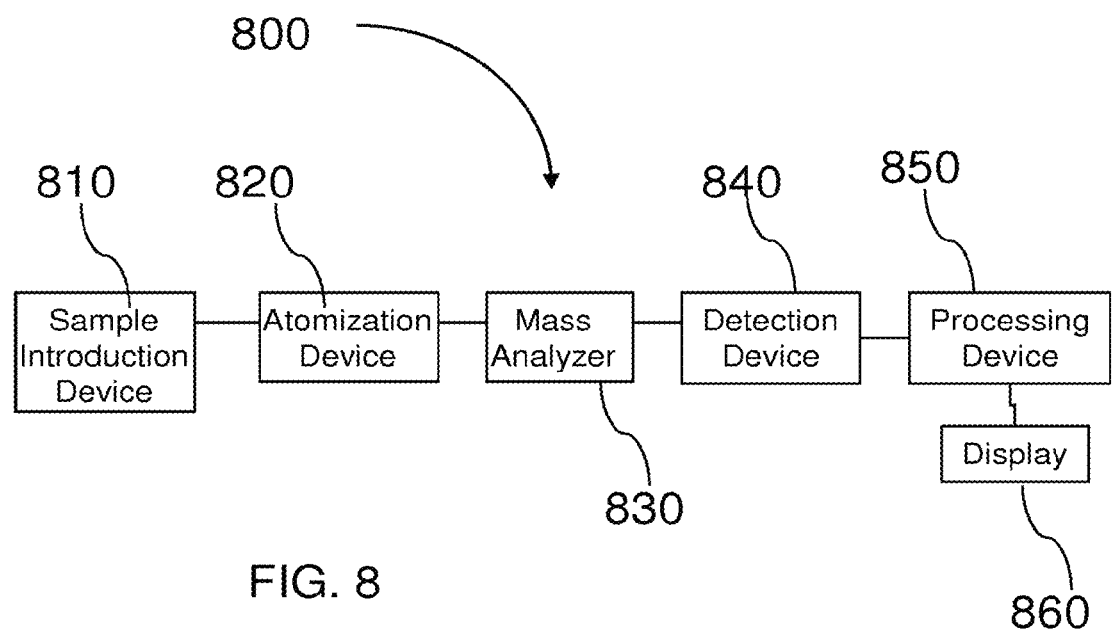
FIG. 8 is a block diagram of a mass spectrometer, in accordance with certain examples.

In certain embodiments, the oxidation resistant induction devices described herein can be used in a mass spectrometer. When the oxidation resistant induction devices are used in a mass spectrometer, there can be a reduced chance of oxide formation and a reduced likelihood of contamination from such oxides. An illustrative MS device is shown in FIG. 8. The MS device 800 includes a sample introduction device 810, an atomization device 820, a mass analyzer 830, a detection device 840, a processing device 850 and a display 860. The sample introduction device 810, the atomization device 820, the mass analyzer 830 and the detection device 840 may be operated at reduced pressures using one or more vacuum pumps. In certain examples, however, only the mass analyzer 830 and the detection device 840 may be operated at reduced pressures. The sample introduction device 810 may include an inlet system configured to provide sample to the atomization device 820. The inlet system may include one or more batch inlets, direct probe inlets and/or chromatographic inlets. The sample introduction device 810 may be an injector, a nebulizer or other suitable devices that may deliver solid, liquid or gaseous samples to the atomization device 820. If desired, the sample introduction device 810 can include a low-flow injector as described in reference to FIGS. 5-7. The atomization device 820 may be a device including an oxidation resistant induction device such as, for example, an inductively coupled plasma device that includes an oxidation resistant induction device as discussed herein. Any torch present in the atomization device 820 may be a conventional plasma torch or may be a low-flow plasma torch as described in reference to FIGS. 5-7. The mass analyzer 830 may take numerous forms depending generally on the sample nature, desired resolution, etc., and exemplary mass analyzers are discussed further below. The detection device 840 may be any suitable detection device that may be used with existing mass spectrometers, e.g., electron multipliers, Faraday cups, coated photographic plates, scintillation detectors, etc., and other suitable devices that will be selected by the person of ordinary skill in the art, given the benefit of this disclosure. The processing device 850 typically includes a microprocessor and/or computer and suitable software for analysis of samples introduced into MS device 800. One or more databases may be accessed by the processing device 850 for determination of the chemical identity of species introduced into MS device 800. Other suitable additional devices known in the art may also be used with the MS device 2000 including, but not limited to, autosamplers, such as AS-90plus and AS-93plus autosamplers commercially available from PerkinElmer Health Sciences, Inc.

In certain examples, the mass analyzer 830 of the MS device 800 may take numerous forms depending on the desired resolution and the nature of the introduced sample. In certain examples, the mass analyzer is a scanning mass analyzer, a magnetic sector analyzer (e.g., for use in single and double-focusing MS devices), a quadrupole mass analyzer, an ion trap analyzer (e.g., cyclotrons, quadrupole ions traps), time-of-flight analyzers (e.g., matrix-assisted laser desorbed ionization time of flight analyzers), and other suitable mass analyzers that may separate species with different mass-to-charge ratios. The oxidation resistant induction devices may be used in MS devices that include many different types of ionization methods. For example, electron impact sources, chemical ionization sources, field ionization sources, desorption sources such as, for example, those sources configured for fast atom bombardment, field desorption, laser desorption, plasma desorption, thermal desorption, electrohydrodynamic ionization/desorption, etc., can be used. In yet other examples, thermospray ionization sources, electrospray ionization sources or other ionization sources and devices commonly used in mass spectroscopy can be used with the oxidation resistant induction devices described herein.

In some examples, the MS devices disclosed herein may be hyphenated with one or more other analytical techniques. For example, MS devices may be hyphenated with devices for performing liquid chromatography, gas chromatography, capillary electrophoresis, and other suitable separation techniques. When coupling an MS device with a gas chromatograph, it may be desirable to include a suitable interface, e.g., traps, jet separators, etc., to introduce sample into the MS device from the gas chromatograph. When coupling an MS device to a liquid chromatograph, it may also be desirable to include a suitable interface to account for the differences in volume used in liquid chromatography and mass spectroscopy. For example, split interfaces may be used so that only a small amount of sample exiting the liquid chromatograph may be introduced into the MS device. Sample exiting from the liquid chromatograph may also be deposited in suitable wires, cups or chambers for transport to the atomization devices of the MS device. In certain examples, the liquid chromatograph may include a thermospray configured to vaporize and aerosolize sample as it passes through a heated capillary tube. Other suitable devices for introducing liquid samples from a liquid chromatograph into a MS device will be readily selected by the person of ordinary skill in the art, given the benefit of this disclosure. In certain examples, MS devices, at least one of which includes an oxidation resistant induction device, can be hyphenated with each other for tandem mass spectroscopy analyses. For example, one MS device may include a first type of mass analyzer and the second MS device may include a different or similar mass analyzer as the first MS device. In other examples, the first MS device may be operative to isolate the molecular ions, and the second MS device may be operative to fragment/detect the isolated molecular ions. It will be within the ability of the person of ordinary skill in the art, given the benefit of this disclosure, to design hyphenated MS/MS devices at least one of which includes an oxidation resistant induction device.

In some examples, the oxidation resistant materials can be used in a boost device as described, for example, in U.S. patent application Ser. No. 11/156,274 filed on Jun. 17, 2005, the entire disclosure of which is hereby incorporated herein by reference for all purposes. In certain embodiments, the boost device can be configured as a coiled wire that is produced using an oxidation resistant material such as, for example, aluminum, gold or silver. In some examples, the boost device comprises a coil of wire that comprises an aluminum alloy, that consists essentially of an aluminum alloy or that consists of an aluminum alloy.

Certain specific examples are described in more detail below to illustrate further some of the aspects and features of the technology described herein.

Example 1

Figures 9A, 9B:
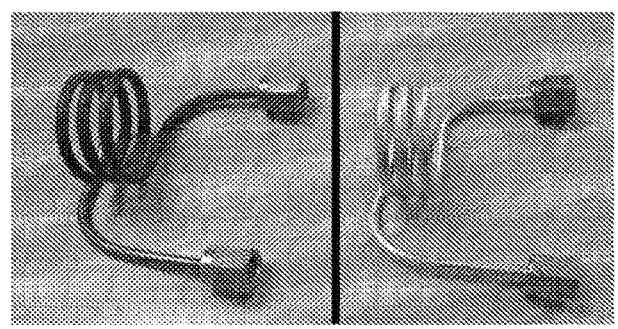
FIG. 9A is a photograph of a copper induction coil showing copper oxide formation and FIG. 9B is a photograph of an aluminum alloy induction coil, in accordance with certain examples.
Figure 10:
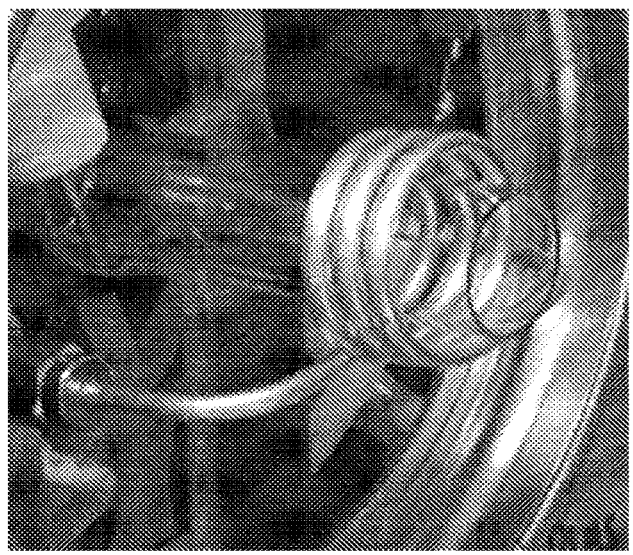
FIG. 10 is a photograph showing an aluminum alloy induction coil positioned around a plasma torch, in accordance with certain examples.
Figure 11:
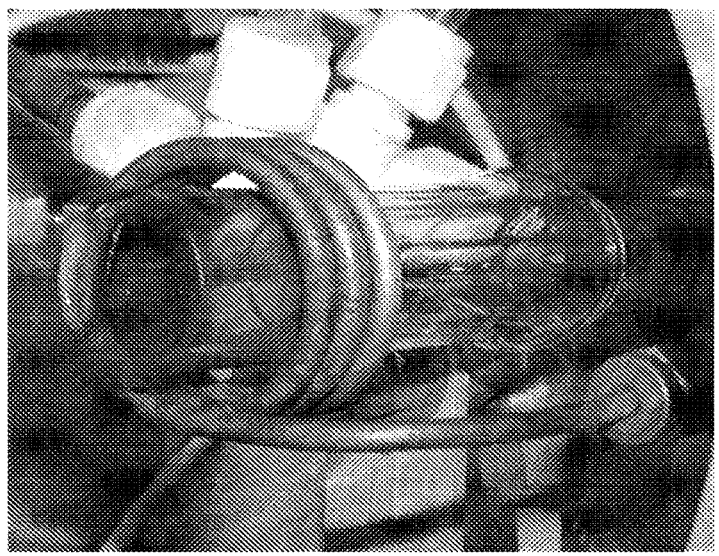
FIG. 11 is a photograph showing a copper induction coil having an oxidized surface and positioned around a plasma torch, in accordance with certain examples.

FIG. 9A and FIG. 11 shows normal oxidation of a copper load coil. This oxidation can become excessive over time and lead to failure of the load coil. FIG. 9B and FIG. 10 shows an aluminum load coil made from a 3003 alloy (commercially available from McMaster-Carr (www.mcmaster.com) which was tested for 100 hours at maximum power. Typically the load coils are both externally and internally cooled. The test instrument used argon gas to internally cool the coil. This argon is then passed through the torch and is used to sustain the plasma. The argon cooling rate was 20 liters/minute with 100 cfm of air passing through the torch box, which also aids in the cooling of the coil. The instrument used was a NexION 300 commercially available from PerkinElmer Health Sciences, Inc.

The aluminum coil exhibited similar qualities as the copper load coil such as ease of ignition, stability, plasma coupling, plasma power and temperature, plasma positioning in the load coil, and sample loading, at least to a first order. The 3003 alloy which was tested was 97.1% pure with manganese being the major additive for strength. A 1000 series alloy (99.5% purity or higher) could be used in place of the 3003 alloy or other suitable oxidation resistant materials can be used.

Tables 1 and 2 below show representative data obtained using the aluminum load coil in the device described above.

TABLE I

| Analyte | Mass | Meas. Intens. Mean | Net Intens. Mean | Net Intens. SD | Net Intens. RSD |
|---|---|---|---|---|---|
| Be | 9 | 6918.9 | 6918.875 | 75.779 | 1.1 |
| Mg | 24 | 37925.9 | 37925.877 | 152.754 | 0.4 |
| Ce++ | 70 | 2132.8 | 0.019 | 0 | 1.5 |
| Ce | 139.9 | 111612.1 | 111612.07 | 1023.113 | 0.9 |
| CeO | 155.9 | 2405.9 | 0.022 | 0 | 1.1 |
| In | 114.9 | 102020 | 102019.997 | 615.972 | 0.6 |
| U | 238.1 | 40971.3 | 40971.338 | 291.428 | 0.7 |
| Bkgd | 220 | 0.5 | 0.533 | 0.845 | 158.4 |
| Bkgd | 8 | 2 | 1.967 | 0.877 | 44.6 |

TABLE 2

| Analyte | Mass | Meas. Intens. Mean | Net Intens. Mean | Net Intens. SD | Net Intens. RSD |
|---|---|---|---|---|---|
| Be | 9 | 5314.9 | 5314.889 | 82.575 | 1.6 |
| Mg | 24 | 29817.8 | 29817.786 | 115.274 | 0.4 |
| Ce++ | 70 | 1286.8 | 0.013 | 0 | 2.1 |
| Ce | 139.9 | 100726 | 100725.968 | 733.177 | 0.7 |

TABLE 2-continued

| Analyte | Mass | Meas. Intens. Mean | Net Intens. Mean | Net Intens. SD | Net Intens. RSD |
|---|---|---|---|---|---|
| CeO | 155.9 | 1594.7 | 0.016 | 0 | 1.1 |
| In | 114.9 | 82676.5 | 82676.459 | 622.519 | 0.8 |
| U | 238.1 | 36230.7 | 36230.686 | 209.523 | 0.6 |
| Bkgd | 220 | 0.1 | 0.05 | 0.112 | 223.6 |
| Bkgd | 8 | 1.7 | 1.65 | 0.894 | 54.2 |

The obtained measurements were consistent with those that can be obtained using a copper load coil. However, no substantial oxidation was visually observed on the aluminum alloy induction device. These results are consistent with an oxidation resistant induction device providing at least comparable results as a copper induction coil while at the same time not suffering from substantial unwanted oxidation.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method of generating a plasma comprising:
introducing a gas into a torch body;
providing radio frequency energy to the torch using an induction device comprising an oxidation resistant material, in which the induction device is configured as a helical induction coil comprising a plurality of coil turns coupled to each other, in which the coil turns comprise an effective amount of the oxidation resistant material to permit a plasma to be sustained in the torch body for at least ten hours without substantial oxidation of the helical induction coil;
igniting the gas in the torch body to generate the plasma; and
sustaining the plasma in the torch body for at least ten hours without substantial oxidation of the helical induction coil.

2. The method of claim 1, in which the helical induction coil comprises a non-coated oxidation resistant material.

3. The method of claim 1, in which the helical induction coil consists essentially of an aluminum alloy.

4. The method of claim 1, further comprising sustaining the plasma in the torch body for at least one hundred hours without substantial oxidation forming on the helical induction coil.

5. A method of generating a plasma comprising:
introducing a gas into a torch body;
providing radio frequency energy to the torch using an induction device comprising an oxidation resistant paramagnetic material, in which the induction device is configured as a helical induction coil comprising a plurality of coil turns coupled to each other, in which the coil turns comprise an effective amount of the oxidation resistant paramagnetic material to permit a plasma to be sustained in the torch body for at least ten hours without substantial oxidation of the helical induction coil;
igniting the gas in the torch body to generate the plasma; and
sustaining the plasma in the torch body for at least ten hours without substantial oxidation of the helical induction coil.

6. The method of claim 5, in which the helical induction coil comprises a non-coated oxidation resistant paramagnetic material.

7. The method of claim 5, in which the helical induction coil consists essentially of an aluminum alloy.

8. The method of claim 5, further comprising sustaining the plasma in the torch body for at least one hundred hours without substantial oxidation forming on the induction device.

9. The method of claim 1, further comprising configuring the helical induction coil device to comprise one and one half turns to ten turns.

10. The method of claim 9, in which the helical induction coil comprises at least 97% by weight of the oxidation resistant material.

11. The method of claim 1, further comprising configuring the helical induction coil to comprise two and one half turns.

12. The method of claim 11, in which the helical induction coil comprises at least 97% by weight of the oxidation resistant material.

13. The method of claim 5, further comprising configuring the helical induction coil to comprise one and one half turns to ten turns.

14. The method of claim 13, in which the helical induction coil comprises at least 97% by weight of the oxidation resistant paramagnetic material.

15. The method of claim 5, further comprising configuring the helical induction coil to comprise two and one half turns to six turns.

16. The method of claim 15, in which the helical induction coil comprises at least 97% by weight of the oxidation resistant paramagnetic material.

17. The method of claim 1, further comprising externally cooling the helical induction coil with argon and air.

18. The method of claim 17, further comprising internally cooling the helical induction coil with argon.

19. The method of claim 5, further comprising externally cooling the helical induction coil with argon and air.

20. The method of claim 19, further comprising internally cooling the helical induction coil with argon.

* * * * *